(12) United States Patent
Mugler, III et al.

(10) Patent No.: US 10,718,837 B2
(45) Date of Patent: Jul. 21, 2020

(54) 3D UTE IMAGING USING VARIABLE-TE STACK-OF-SPIRALS ACQUISITION

(71) Applicants: UNIVERSITY OF VIRGINIA PATENT FOUNDATION, Charlottesville, VA (US); Siemens Healthcare GmbH, Erlangen (DE)

(72) Inventors: John P. Mugler, III, Charlottesville, VA (US); Samuel W. Fielden, Lewisburg, PA (US); G. Wilson Miller, IV, Charlottesville, VA (US); Craig H. Meyer, Charlottesville, VA (US); Talissa A. Altes, Philadelphia, PA (US); Alto Stemmer, Erlangen (DE); Josef Pfeuffer, Erlangen (DE); Berthold Kiefer, Erlangen (DE)

(73) Assignees: UNIVERSITY OF VIRGINIA PATENT FOUNDATION, Charlottesville, VA (US); SIEMENS HEALTHCARE GMBH, Erlangen (DE)

( * ) Notice: Subject to any disclaimer, the term of this patent is extended or adjusted under 35 U.S.C. 154(b) by 351 days.

(21) Appl. No.: 15/493,842

(22) Filed: Apr. 21, 2017

(65) Prior Publication Data
US 2017/0307705 A1 Oct. 26, 2017

Related U.S. Application Data

(60) Provisional application No. 62/335,389, filed on May 12, 2016, provisional application No. 62/325,800, filed on Apr. 21, 2016.

(51) Int. Cl.
*G01R 33/48* (2006.01)
*A61B 5/00* (2006.01)
*A61B 5/055* (2006.01)

(52) U.S. Cl.
CPC ......... *G01R 33/4816* (2013.01); *A61B 5/004* (2013.01); *A61B 5/055* (2013.01);
(Continued)

(58) Field of Classification Search
CPC ...... G01R 33/4816; A61B 5/004; A61B 5/055
See application file for complete search history.

(56) References Cited

U.S. PATENT DOCUMENTS

| 8,386,013 | B2 * | 2/2013 | Du | G01R 33/4824 |
| | | | | 324/307 |
| 9,322,896 | B2 | 4/2016 | Fielden et al. | |

(Continued)

OTHER PUBLICATIONS

Chang, E.Y., et al., "UTE Imaging in the Musculoskeletal System," Journal of Magnetic Resonance Imaging, 2015, vol. 41; pp. 870-833.

(Continued)

*Primary Examiner* — Dixomara Vargas (57) ABSTRACT

Some aspects of the present disclosure relate to ultrashort-echo-time (UTE) imaging. In one embodiment, a method includes acquiring UTE imaging data associated with an area of interest of a subject. The acquiring comprises applying an imaging pulse sequence with a three-dimensional (3D) spiral acquisition and a nonselective excitation pulse. The method also includes reconstructing at least one image of the area of interest from the acquired UTE imaging data.

25 Claims, 9 Drawing Sheets

(52) U.S. Cl.
CPC ........... *A61B 5/4504* (2013.01); *A61B 5/4514* (2013.01); *A61B 5/4523* (2013.01); *A61B 5/4533* (2013.01); *A61B 2576/02* (2013.01); *G01R 33/4826* (2013.01)

(56) References Cited

U.S. PATENT DOCUMENTS

| | | | | |
|---|---|---|---|---|
| 9,594,139 | B2* | 3/2017 | Wiesinger | G01R 33/5608 |
| 9,594,144 | B2* | 3/2017 | Hardy | G01R 33/4826 |
| 9,651,645 | B2 | 5/2017 | Fielden et al. | |
| 2007/0255129 | A1* | 11/2007 | Du | G01R 33/4824 |
| | | | | 600/410 |
| 2008/0258727 | A1* | 10/2008 | Qian | G01R 33/4816 |
| | | | | 324/312 |
| 2009/0099443 | A1* | 4/2009 | Rahmer | G01R 33/4824 |
| | | | | 600/410 |
| 2010/0231218 | A1* | 9/2010 | Qian | G01R 33/4816 |
| | | | | 324/309 |
| 2014/0364721 | A1* | 12/2014 | Lee | A61B 5/055 |
| | | | | 600/411 |
| 2015/0276906 | A1* | 10/2015 | Wiesinger | G01R 33/5608 |
| | | | | 324/309 |
| 2015/0309148 | A1* | 10/2015 | Hardy | G01R 33/4826 |
| | | | | 324/309 |
| 2015/0316630 | A1 | 11/2015 | Zhao et al. | |
| 2016/0148378 | A1 | 5/2016 | Salerno et al. | |
| 2017/0102439 | A1* | 4/2017 | McMillan | G01R 33/56572 |
| 2017/0219672 | A1* | 8/2017 | Miyazaki | G01R 33/4816 |
| 2017/0356972 | A1* | 12/2017 | Wheaton | G01R 33/3854 |

OTHER PUBLICATIONS

Du, J., et al., "Qualitative and Quantitative Ultrashort-TE MRI of Cortical Bone," NMR Biomed., 2013, vol. 26, No. 5, 43 pages.

Johnson, K.M., et al., "Optimized 3D Ultrashort Echo Time Pulmonary MRI," 2013, Magnetic Resonance in Medicine, vol. 70, pp. 1241-1250.

Miller, G.W., et al., "Advances in Functional and Structural Imaging of the Human Lung Using Proton MRI," 2014, vol. 27, No. 12; 34 pages.

Mugler, III, J.P., et al., "Breath-Hold UTE Lung Imaging Using a Stack-of-Spirals Acquisition," 2015, Proc. Intl. Soc. Mag. Reson. Med., vol. 23, p. 1476.

Qian, Y., et al., "Acquisition-Weighted Stack of Spirals for Fast High-Resolution Three Dimensional Ultra-Short Echo Time MR Imaging," 2008, vol. 60, pp. 135-145.

Qian, Y., et al., "High-Resolution Ultrashort Echo Time (UTE) Imaging on Human Knee With Awsos Sequence at 3.o T," 2012, Journal of Magnetic Resonance Imaging, vol. 35, pp. 204-210.

Rahmer, J., et al., "Three-Dimensional Radial Ultrashort Echo-Time Imaging with T2 Adapted Sampling," 2006, Magnetic Resonance in Medicine, vol. 55, pp. 1075-1082.

Tyler, D.J., et al., "Magnetic Resonance Imaging With Ultrashort TE (UTE) PULSE Sequences: Technical Considerations," 2007, Journal of Magnetic Resonance Imaging, vol. 25, pp. 279-289.

Edelman, R. R. et al., Clinical Magnetic Resonance Imaging, Saunders Elsevier, 2006, p. 28.

* cited by examiner

3D UTE IMAGING USING VARIABLE-TE STACK-OF-SPIRALS ACQUISITION

CROSS-REFERENCE TO RELATED APPLICATIONS

This application claims priority to and benefit of U.S. Provisional Patent Application Nos. 62/325,800, filed Apr. 21, 2016, and 62/335,389, filed May 12, 2016, each of which is hereby incorporated by reference herein in its entirety as if fully set forth below.

BACKGROUND

In magnetic resonance imaging (MRI), many biological tissues exhibit such short relaxation times that their signals decay completely by the time conventional sequences begin sampling. For this reason, many parts of the body, such as bone, cartilage, ligaments, and tendons of the musculoskeletal system, and the lungs, can be difficult to study using MRI. Ultrashort-echo-time (UTE) pulse sequences have been developed to begin sampling as closely as possible to the excitation pulse. The time delay caused by the slice selection gradient has led to the development of specialized RF pulses and acquisition schemes for two-dimensional (2D) imaging. However, these methods can be inherently challenging and may have limited robustness. Some alternate implementations of UTE sequences are based on three-dimensional (3D) radial acquisitions. 3D radial acquisition schemes can be slow, often requiring several minutes to collect a full 3D volume of data.

It is with respect to these and other considerations that the various embodiments described below are presented.

SUMMARY

Some aspects of the present disclosure relate to ultrashort-echo-time (UTE) imaging. Some disclosed embodiments relate to UTE imaging of an area of interest of a subject using a 3D stack-of-spirals acquisition with a nonselective exitation pulse, and which can utilize a 3D spoiled gradient-echo sequence. The 3D stack-of-spirals acquisition can achieve short echo times by beginning each spiral readout immediately after the through-plane phase-encoding gradient waveform has completed, resulting in a variable echo time (TE) in the through-plane direction.

In one aspect, the present disclosure relates to method for ultrashort-echo-time (UTE). In one embodiment, the method comprises acquiring UTE imaging data associated with an area of interest of a subject. The acquiring comprises applying an imaging pulse sequence with a three-dimensional (3D) spiral acquisition and a nonselective excitation pulse. The method also includes reconstructing at least one image of the area of interest from the acquired UTE imaging data.

In another aspect, the present disclosure relates to a system for ultrashort-echo-time (UTE) imaging. In one embodiment, the system includes a data acquisition device configured to acquire UTE imaging data associated with an area of interest of a subject. The acquiring comprises applying an imaging pulse sequence with a three-dimensional (3D) spiral acquisition and a nonselective excitation pulse. The system also includes one or more processors coupled to the data acquisition device and configured to cause the system to perform functions that comprise reconstructing at least one image of the area of interest from the acquired UTE imaging data.

In another aspect, the present disclosure relates to a non-transitory computer-readable medium having stored instructions that, when executed by one or more processors, cause one or more computing devices to perform specific functions for ultrashort-echo-time (UTE) imaging. In one embodiment, the specific functions performed include acquiring UTE imaging data associated with an area of interest of a subject. The acquiring comprises applying an imaging pulse sequence with a three-dimensional (3D) spiral acquisition and a nonselective excitation pulse. The specific functions performed by the one or more computing devices also comprise reconstructing at least one image of the area of interest from the acquired UTE imaging data.

Other aspects and features according to the present disclosure will become apparent to those of ordinary skill in the art, upon reviewing the following detailed description in conjunction with the accompanying figures.

BRIEF DESCRIPTION OF THE DRAWINGS

Reference will now be made to the accompanying drawings, which are not necessarily drawn to scale.

DETAILED DESCRIPTION

Some aspects of the present disclosure relate to ultrashort-echo-time (UTE) imaging. Some disclosed embodiments relate to UTE imaging of an area of interest of a subject using a UTE acquisition based on a 3D stack-of-spirals acquisition with a nonselective RF pulse, and which can utilize a 3D spoiled gradient-echo sequence.

A 3D stack-of-spirals acquisition according to some embodiments of the present disclosure can achieve very short echo times by beginning each spiral readout immediately after the through-plane phase-encoding gradient waveform has completed, resulting in a variable TE in the through-plane direction. This can minimize the duration of each through-plane phase encoding (PE) gradient waveform while simultaneously minimizing the TE such that, in the center of k-space, the minimum TE is limited only by RF excitation events or hardware switching delays, and increases toward the edges of k-space along the through-plane PE direction.

In the past, some approaches to 3D UTE have used a slab-selective pulse to restrict the number of 3D phase encoding lines that would need to be collected. In some embodiments of the present disclosure, instead of a slab-selective excitation pulse, a short nonselective hard RF pulse is used, which can greatly reduce the minimum TE. For the center of k-space where the phase encoding (PE) gradients are small (or nonexistent), the minimum TE achievable can, in accordance with some example implementations of the present disclosure, be reduced to as low as 50 μs. Furthermore, the efficiency of the spiral readouts, in requiring shorter total acquisition times, provides for the rapid generation of volumetric UTE images. Example implementations described herein demonstrate the utility of UTE imaging in accordance with some embodiments for visualizing areas of interest of a subject, for instance the head, knee, and lungs of human subjects.

Implementing imaging techniques in accordance with various aspects of the present disclosure described herein can be used for determining physical or physiological conditions or various characteristics of an area of interest of a subject. For example, reconstructed images from UTE sequences implemented in accordance with certain embodiments of the present disclosure can be used for detecting, based on the images, whether an area of the musculoskeletal system or organs have an injury (e.g., fracture of a bone, impairment to a ligament or tendon), abnormality (e.g., abnormal size, degeneration, calcification, presence of an abnormal spot such as a nodule in the lungs or other organs or tissue) or other type of conditions to be analyzed or diagnosed.

Although example embodiments of the present disclosure are explained in detail herein, it is to be understood that other embodiments are contemplated. Accordingly, it is not intended that the present disclosure be limited in its scope to the details of construction and arrangement of components set forth in the following description or illustrated in the drawings. The present disclosure is capable of other embodiments and of being practiced or carried out in various ways.

It must also be noted that, as used in the specification and the appended claims, the singular forms "a," "an" and "the" include plural referents unless the context clearly dictates otherwise. Certain values and/or ranges may be expressed in terms of "about" or "approximately" a value or range. For example, a range may be from "about" or "approximately" one particular value to "about" or "approximately" another particular value. When such a range is expressed, other exemplary embodiments include from the one particular value and/or to the other particular value. As used herein, "about" means within 20 percent or closer of a given value or range.

By "comprising" or "containing" or "including" is meant that at least the named compound, element, particle, or method step is present in the composition or article or method, but does not exclude the presence of other compounds, materials, particles, method steps, even if the other such compounds, material, particles, method steps have the same function as what is named.

In describing example embodiments, terminology will be resorted to for the sake of clarity. It is intended that each term contemplates its broadest meaning as understood by those skilled in the art and includes all technical equivalents that operate in a similar manner to accomplish a similar purpose. It is also to be understood that the mention of one or more steps of a method does not preclude the presence of additional method steps or intervening method steps between those steps expressly identified. Steps of a method may be performed in a different order than those described herein without departing from the scope of the present disclosure. Similarly, it is also to be understood that the mention of one or more components in a device or system does not preclude the presence of additional components or intervening components between those components expressly identified.

As discussed herein, a "subject" or "patient" may be any applicable human, animal, or other organism, living or dead, or other biological or molecular structure or chemical environment, and may relate to particular components of the subject, for instance specific organs, bones, tissues, or fluids (e.g., human tissue in a particular area of the body of a living subject), which may be in a particular location of the subject referred to herein as an "area of interest" or a "region of interest."

A detailed description of aspects of the present disclosure will now be provided with reference to the accompanying drawings. The drawings form a part hereof and show, by way of illustration, specific embodiments or examples. In referring to the drawings, like numerals represent like elements throughout the several figures.

Figure 1:
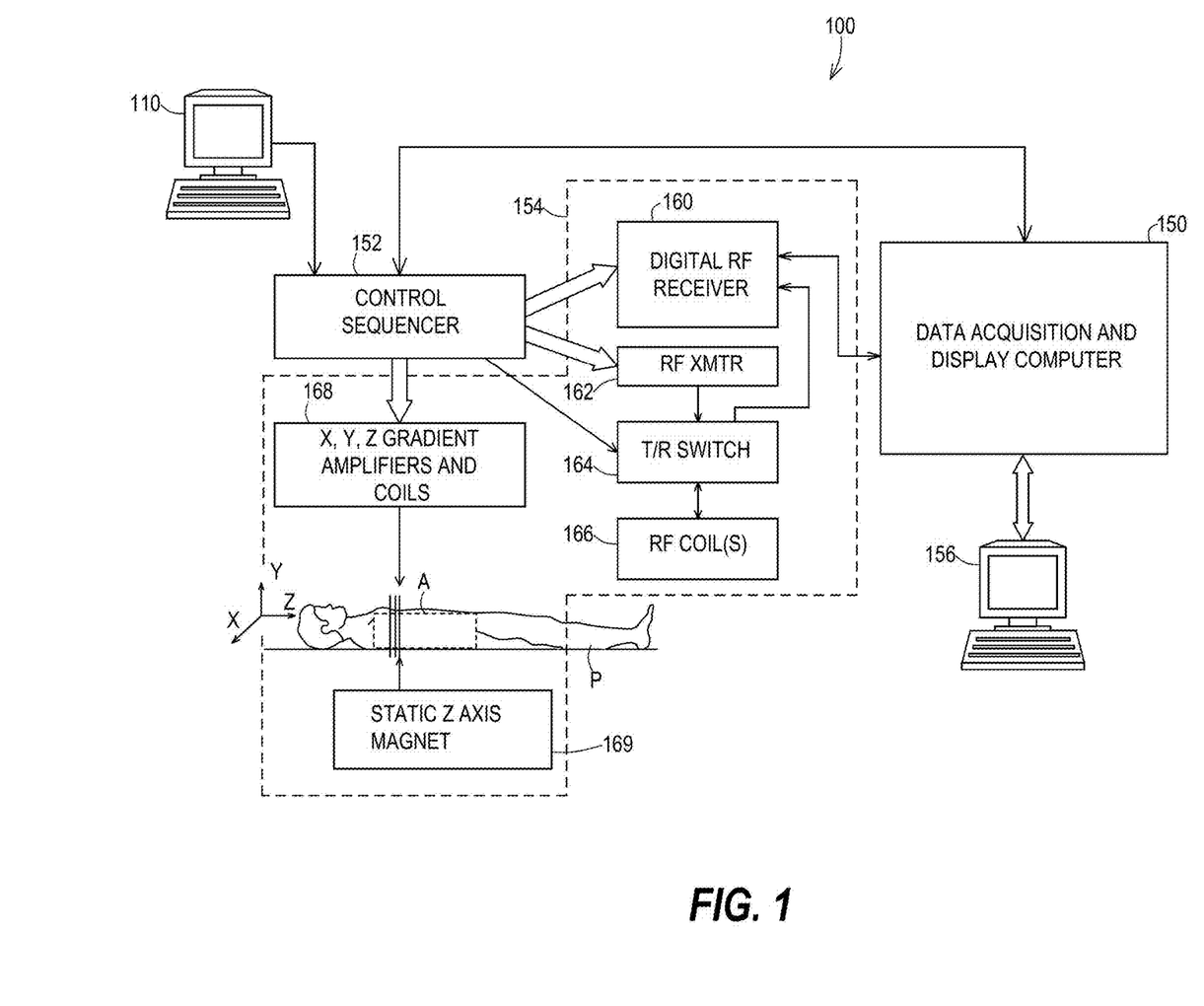
FIG. 1 is a system diagram illustrating an imaging system capable of implementing aspects of the present disclosure in accordance with one or more embodiments.

FIG. 1 is a system diagram illustrating an operating environment capable of implementing aspects of the present disclosure in accordance with one or more example embodiments. FIG. 1 illustrates an example of a magnetic resonance imaging (MRI) system 100, including a data acquisition and display computer 150 coupled to an operator console 110, an MRI real-time control sequencer 152, and an MRI subsystem 154. The MRI subsystem 154 may include XYZ magnetic gradient coils and associated amplifiers 168, a static Z-axis magnet 169, a digital RF transmitter 162, a digital RF receiver 160, a transmit/receive switch 164, and RF coil(s) 166. The MRI subsystem 154 may be controlled in real time by control sequencer 152 to generate magnetic and radio frequency fields that stimulate magnetic resonance phenomena in a subject P to be imaged, for example to implement magnetic resonance imaging sequences in accordance with various embodiments of the present disclosure. A contrast-enhanced image of an area of interest A of the subject P (which may also be referred to herein as a "region of interest") may be shown on display 156. The display 156 may be implemented through a variety of output interfaces, including a monitor, printer, or data storage.

The area of interest A corresponds to a region associated with one or more physiological activities in subject P. The area of interest shown in the example embodiment of FIG. 1 corresponds to a chest region of subject P, but it should be appreciated that the area of interest for purposes of implementing various aspects of the disclosure presented herein is not limited to the chest area. It should be recognized and appreciated that the area of interest in various embodiments may encompass various areas of subject P associated with various physiological characteristics, activities, and conditions, such as, but not limited to those associated with the heart region, brain region, lungs, upper or lower extremities, or other organs or tissues. For example, various aspects of the present disclosure are described herein as being implemented in imaging parts of the musculoskeletal system and the lungs of human subjects.

It should be appreciated that any number and type of computer-based medical imaging systems or components, including various types of commercially available medical imaging systems and components, may be used to practice certain aspects of the present disclosure. Systems as described herein with respect to example embodiments are not intended to be specifically limited to the particular system shown in FIG. 1.

One or more data acquisition or data collection steps as described herein in accordance with one or more embodiments may include acquiring, collecting, receiving, or otherwise obtaining data such as imaging data corresponding to an area of interest. By way of example, data acquisition or collection may include acquiring data via a data acquisition device, receiving data from an on-site or off-site data acquisition device or from another data collection, storage, or processing device. Similarly, data acquisition or data collection devices of a system in accordance with one or more embodiments of the present disclosure may include any device configured to acquire, collect, or otherwise obtain data, or to receive data from a data acquisition device within the system, an independent data acquisition device located on-site or off-site, or another data collection, storage, or processing device.

Figure 2:
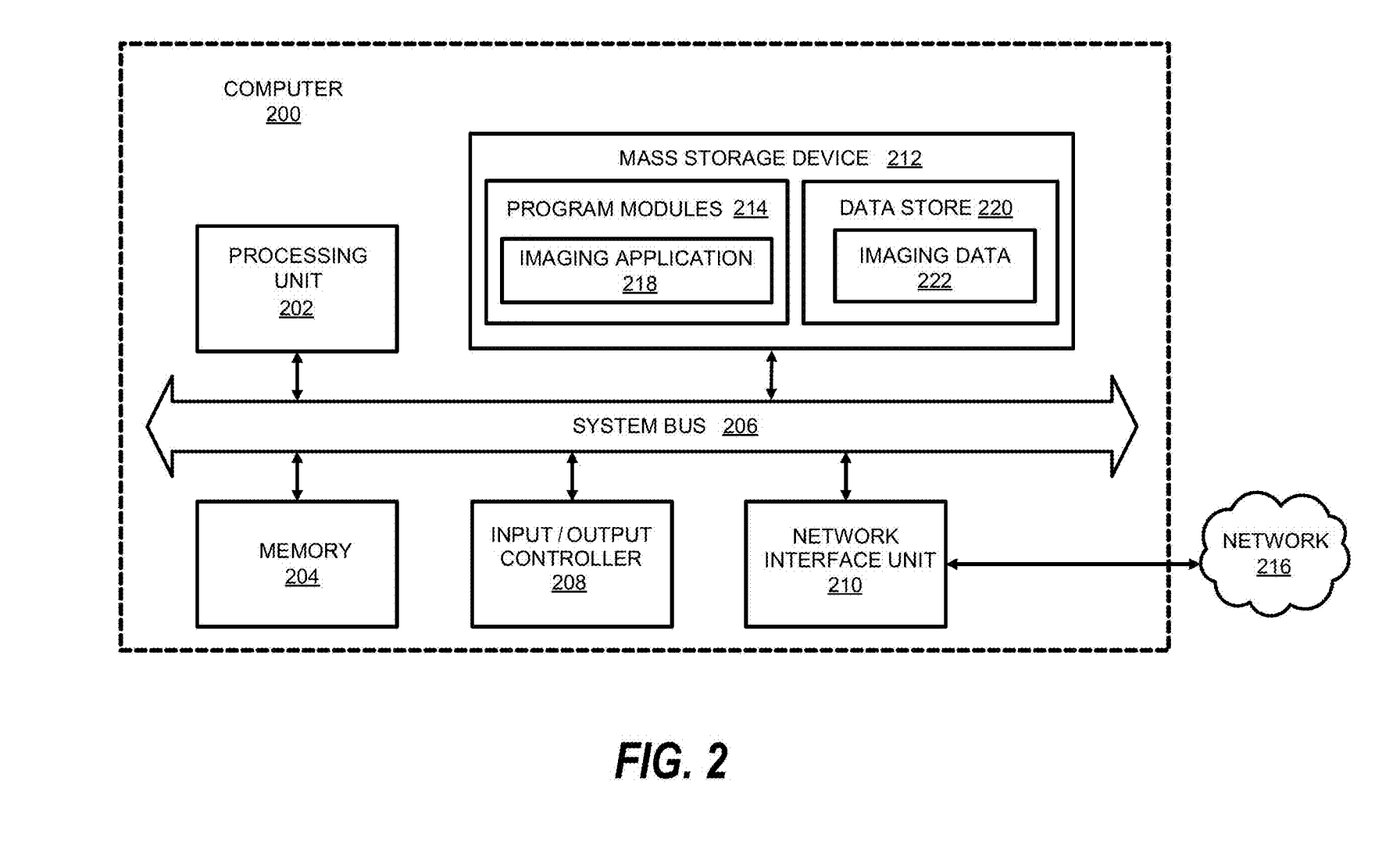
FIG. 2 is a computer architecture diagram showing a computing system capable of implementing aspects of the present disclosure in accordance with one or more embodiments.

FIG. 2 is a computer architecture diagram showing a computing system capable of implementing aspects of the present disclosure in accordance with one or more embodiments described herein. A computer 200 may be configured to perform one or more specific steps of a method and/or specific functions for a system. The computer may be configured to perform one or more functions associated with embodiments illustrated in one or more of FIGS. 3-9. For example, the computer 200 may be configured to perform aspects described herein for implementing the pulse sequence shown in FIG. 3 and for various aspects of obtaining the images shown in FIGS. 4-9. It should be appreciated that the computer 200 may be implemented within a single computing device or a computing system formed with multiple connected computing devices. The computer 200 may be configured to perform various distributed computing tasks, in which processing and/or storage resources may be distributed among the multiple devices. The data acquisition and display computer 150 and/or operator console 110 of the system shown in FIG. 1 may include one or more systems and components of the computer 200.

As shown, the computer 200 includes a processing unit 202 ("CPU"), a system memory 204, and a system bus 206 that couples the memory 204 to the CPU 202. The computer 200 further includes a mass storage device 212 for storing program modules 214. The program modules 214 may be operable to perform functions associated with one or more embodiments described herein. For example, when executed, the program modules can cause one or more medical imaging devices and/or computers to perform functions described herein for implementing the variable-TE 3D spiral pulse sequence shown in FIG. 3 and for various aspects of obtaining the images shown in FIGS. 4-9. The program modules 214 may include an imaging application 218 for performing data acquisition and/or processing functions as described herein, for example to acquire and/or process image data corresponding to magnetic resonance imaging of an area of interest. The computer 200 can include a data store 220 for storing data that may include imaging-related data 222 such as acquired data from the implementation of magnetic resonance imaging pulse sequences in accordance with various embodiments of the present disclosure.

The mass storage device 212 is connected to the CPU 202 through a mass storage controller (not shown) connected to the bus 206. The mass storage device 212 and its associated computer-storage media provide non-volatile storage for the computer 200. Although the description of computer-storage media contained herein refers to a mass storage device, such as a hard disk, it should be appreciated by those skilled in the art that computer-storage media can be any available computer storage media that can be accessed by the computer 200.

By way of example and not limitation, computer storage media (also referred to herein as "computer-readable storage medium" or "computer-readable storage media") may include volatile and non-volatile, removable and non-removable media implemented in any method or technology for storage of information such as computer-storage instructions, data structures, program modules, or other data. For example, computer storage media includes, but is not limited to, RAM, ROM, EPROM, EEPROM, flash memory or other solid state memory technology, CD-ROM, digital versatile disks ("DVD"), HD-DVD, BLU-RAY, or other optical storage, magnetic cassettes, magnetic tape, magnetic disk storage or other magnetic storage devices, or any other medium which can be used to store the desired information and which can be accessed by the computer 200. "Computer storage media", "computer-readable storage medium" or "computer-readable storage media" as described herein do not include transitory signals.

According to various embodiments, the computer 200 may operate in a networked environment using connections to other local or remote computers through a network 216 via a network interface unit 210 connected to the bus 206. The network interface unit 210 may facilitate connection of the computing device inputs and outputs to one or more suitable networks and/or connections such as a local area network (LAN), a wide area network (WAN), the Internet, a cellular network, a radio frequency (RF) network, a Bluetooth-enabled network, a Wi-Fi enabled network, a satellite-based network, or other wired and/or wireless networks for communication with external devices and/or systems.

The computer 200 may also include an input/output controller 208 for receiving and processing input from any of a number of input devices. Input devices may include one or more of keyboards, mice, stylus, touchscreens, microphones, audio capturing devices, and image/video capturing devices. An end user may utilize the input devices to interact with a user interface, for example a graphical user interface, for managing various functions performed by the computer 200. The input/output controller 208 may be configured to manage output to one or more display devices for displaying visually representations of data, such as display monitors/screens that are integral with other components of the computer 200 or remote displays.

The bus 206 may enable the processing unit 202 to read code and/or data to/from the mass storage device 212 or other computer-storage media. The computer-storage media may represent apparatus in the form of storage elements that are implemented using any suitable technology, including but not limited to semiconductors, magnetic materials, optics, or the like. The computer-storage media may represent memory components, whether characterized as RAM, ROM, flash, or other types of technology. The computer storage media may also represent secondary storage, whether implemented as hard drives or otherwise. Hard drive implementations may be characterized as solid state, or may include rotating media storing magnetically-encoded information. The program modules 214, which include the imaging application 218, may include instructions that, when loaded into the processing unit 202 and executed, cause the computer 200 to provide functions associated with one or more embodiments illustrated in FIGS. 3-9. The program modules 214 may also provide various tools or techniques by which the computer 200 may participate within the overall systems or operating environments using the components, flows, and data structures discussed throughout this description.

Now referring to a variable-TE spiral pulse sequence in accordance with some embodiments of the present disclosure, from the excitation event, transverse decay advances rapidly for short T2 species. In some embodiments, each partition is sampled at a different time delay from the RF pulse, and so has a different echo time. The amount of transverse decay that has occurred when each partition is encoded impacts the amplitude of the resulting signal. So the signal intensity is a function of echo time, and it directly follows that the signal intensity changes as a function of k-space partition number. Very short TEs are achievable near the center of k-space, where the through-plane PE gradients are small or nonexistent.

In some embodiments, a 3D spoiled gradient-echo sequence (VIBE, Siemens) is modified to support the stack-of-spirals acquisition, to make room for spiral gradients instead of standard Cartesian readout events, by using a fast, nonselective pulse for excitation and varying the TE depending on the partition-encoding gradient.

Figure 3A:
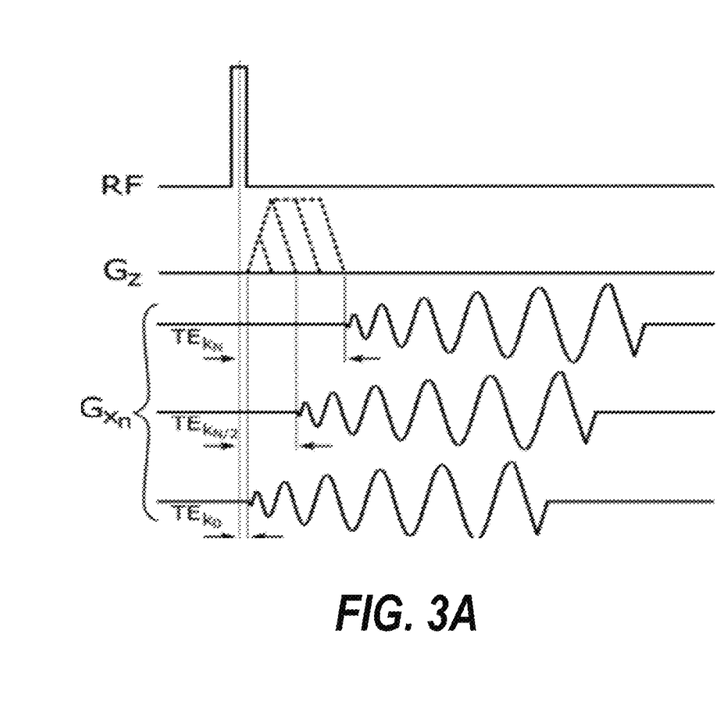
FIGS. 3A and 3B illustrate a variable-TE 3D spiral pulse sequence and spiral interleaves, respectively, in accordance with some embodiments of the present disclosure.
Figure 3B:
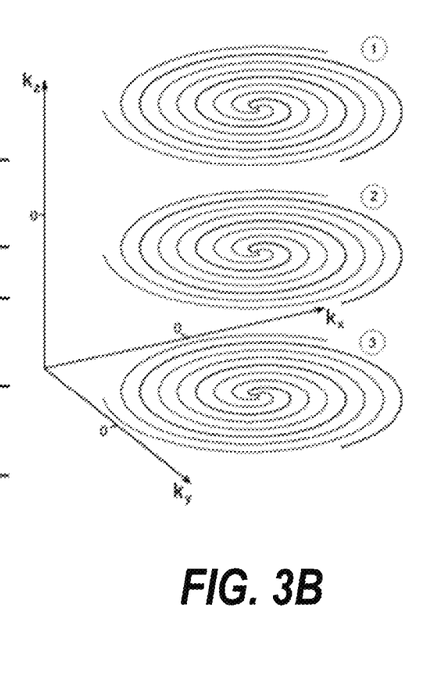

FIG. 3 shows variable-TE spiral pulse sequence (FIG. 3A) and spiral interleaves (FIG. 3B) in accordance with embodiments of the present disclosure for UTE imaging. FIG. 3A illustrates a sequence for acquiring a single spiral interleaf, and FIG. 3B illustrates a "stack" of multiple acquired spiral interleaves. In particular, FIG. 3A shows one repetition time (TR) of a variable-TE stack-of-spirals pulse sequence in accordance with some embodiments of the present disclosure. A hard RF pulse, represented by the top line, begins the sequence of events. The required partition-encoding gradient, called Gz on the second line, is played out immediately thereafter. The gradient is designed to meet the necessary area in as short a time as possible in order to minimize all echo times. Conventionally, all readout events would be aligned in time (i.e., have the same time delay, or echo time, after the RF pulse), but in this method, the spiral readout (Gx) begins as soon as possible after Gz is complete for the given partition. As Gz is incremented to encode further reaches of k-space, Gx must be incrementally delayed, represented by the Gx subscripts. For the center of k-space ($k_0$), the minimum achievable TE can be very short. The maximum extent in k-space is user-selectable ($k_N$), and will have the longest TE.

Various aspects of the present disclosure will now be described with reference to some example implementations and corresponding results and the images of FIGS. 4-9. Some experimental data are presented herein for purposes of illustration and should not be construed as limiting the scope of the present disclosure in any way or excluding any alternative or additional embodiments.

For the first two example implementations described below (with reference to FIGS. 4-7), a 60 μs nonselective hard RF excitation pulse (rectangular RF waveform) was used, reducing the minimum TE to 50 μs. Maximum TE depended on number of slices and slice resolution, and was generally in the range of 250-400 μs. In these implementations, the sequence's operation was demonstrated in two settings: imaging of a human head (FIGS. 4 and 5), and imaging of a human knee (FIGS. 6 and 7).

Figure 4:
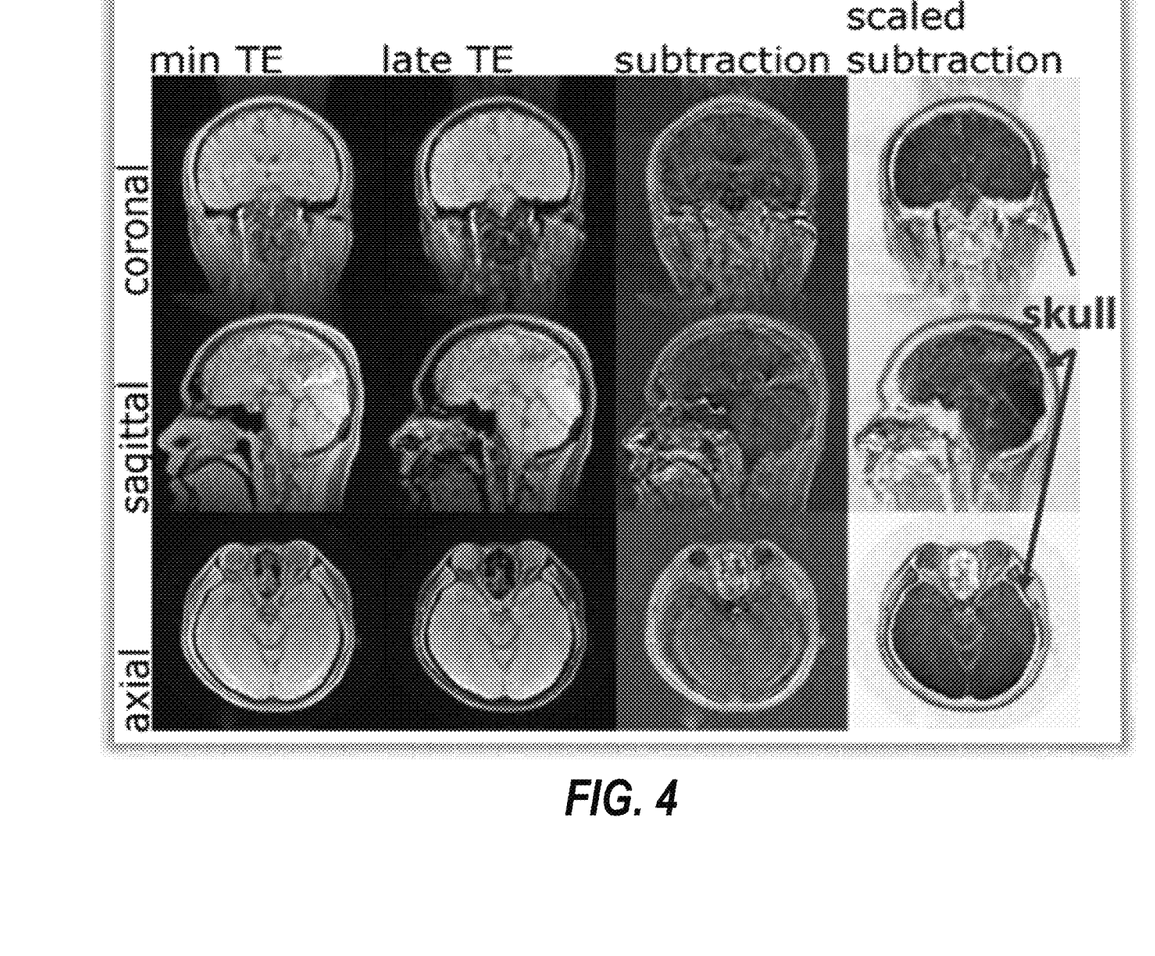
FIG. 4 shows whole-head UTE images obtained by implementing aspects of the present disclosure in accordance with some embodiments.
Figure 5:
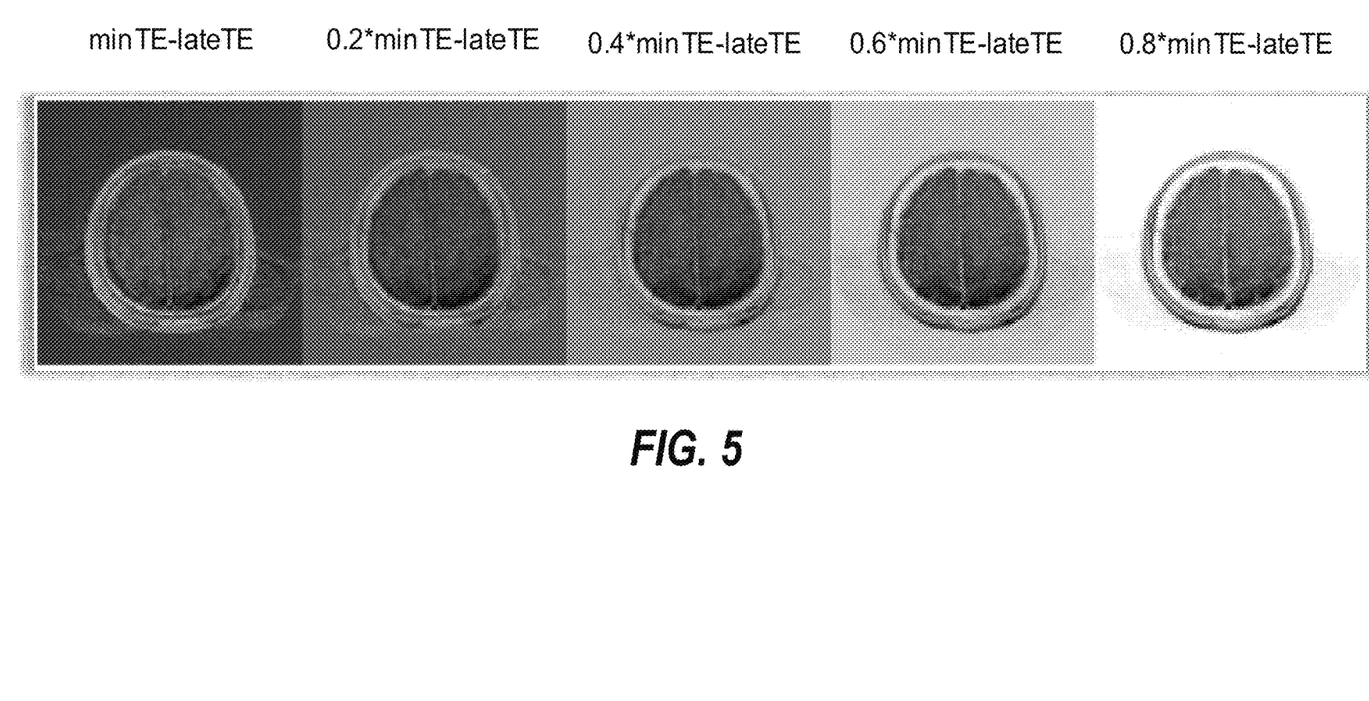
FIG. 5 shows 3D UTE images of a human knee, obtained by implementing aspects of the present disclosure in accordance with some embodiments.

In a first example implementation, a whole human skull was scanned with the following parameters: TR=10 ms; TE=50-370 μs; flip angle 5°; matrix 96×96×64; FOV 240 mm$^3$; 98 interleaves of 1.0 ms duration each; 2 echoes, minTE and lateTE (5.1 ms); 67-second acquisition time. Imaging was performed using a 12-channel head RF coil. A second volumetric image was obtained with a TE of 5.1 ms (to preserve fat/water phase) to provide late-TE comparison images. Two echoes were acquired and they were subtracted to highlight the bone signal. FIG. 4 shows whole-head spiral UTE images alongside late-echo images to illustrate the difference in contrast achievable with UTE imaging sequences described above in accordance with embodiments of the present disclosure. Direct subtractions (see "subtraction" column of images in FIG. 4) as well as scaled subtractions (see "scaled subtraction" column of images in FIG. 4 and row of images in FIG. 5) are also shown, highlighting the bone signal.

Figure 6:
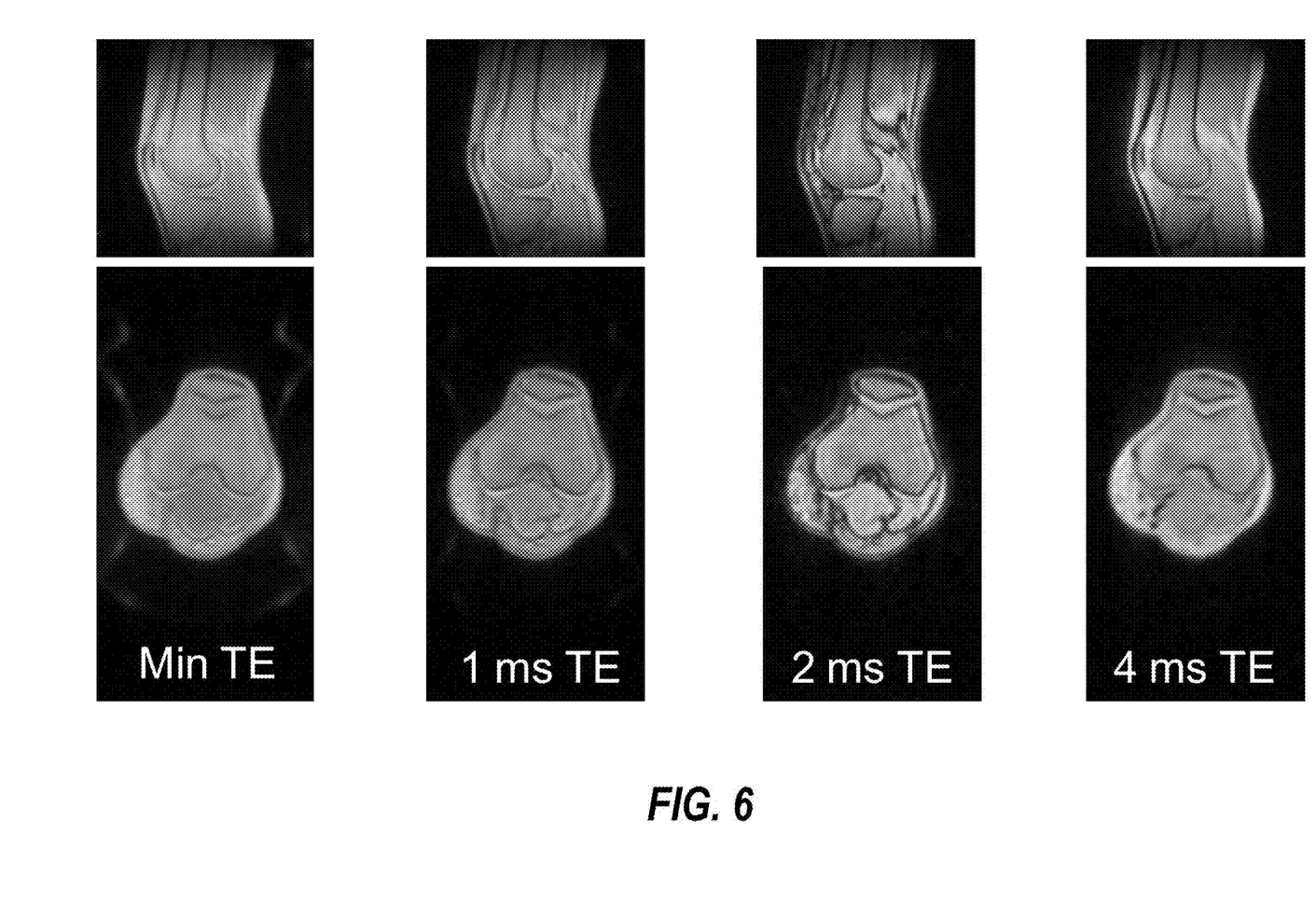
FIG. 6 shows images of a human knee obtained by implementing aspects of the present disclosure in accordance with some embodiments, imaged at multiple TEs and acquired with no fat saturation.
Figure 7:
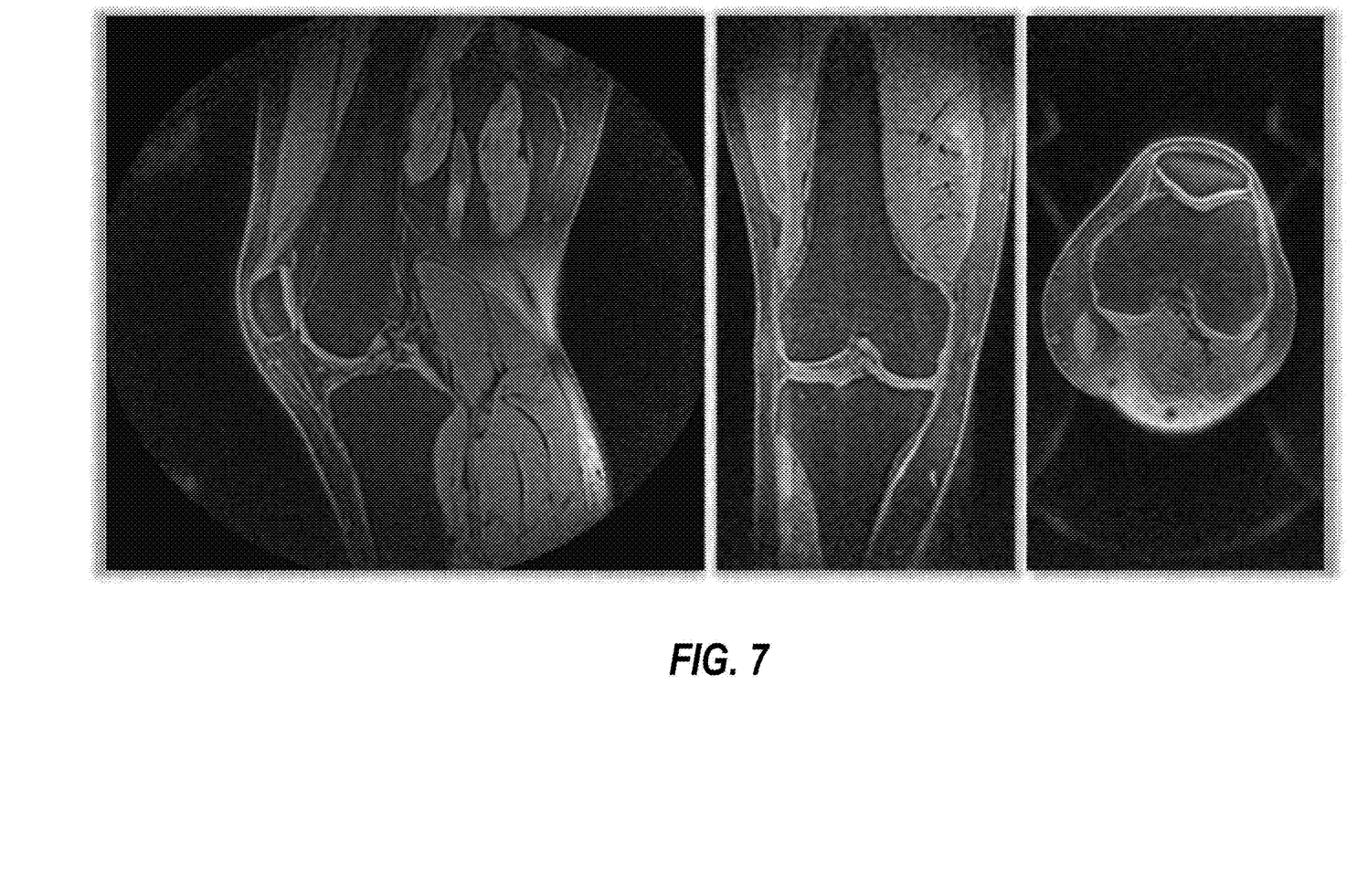
FIG. 7 shows fat suppressed images of a human knee, obtained by implementing aspects of the present disclosure in accordance with some embodiments, showing cartilage and meniscus as a bright signal within the joint.

Now referring to FIGS. 6 and 7, in a second implementation, a human knee was scanned, using an extremity coil, with scan parameters adjusted slightly to achieve true 1.5× 1.5×1.5 mm$^3$ isotropic resolution. The following specific parameters were used: TR=6 ms; TE=50-410 μs; flip angle 5°, matrix 192×192×96; FOV 300 mm$^2$×150 mm; 168 interleaves of 2.5 ms duration each. Because cartilage has a longer T2* than bone, the readout duration was extended to 2.5 ms and the required number of interleaves dropped to 70, resulting in a total acquisition time of 97 seconds. All imaging was performed on a 1.5 T scanner (MAGNETOM Avanto, Siemens Healthcare, Erlangen, Germany). Specifically, FIG. 6 shows the knee imaged at multiple TEs (these images were acquired with no fat saturation), and FIG. 7 shows fat suppressed images of the knee, showing cartilage and meniscus as bright signal within the joint.

Among other benefits and advantages of practicing various aspects of the present disclosure in accordance with the above-mentioned example implementations and results for imaging of the head and knee of a subject (and with reference to FIGS. 4-7), by utilizing non-selective RF pulses, the minimum echo time achievable by a stack-of-spirals UTE sequence can be reduced (from 600 μs to 50 μs in the particular implementations described above), enabling capture of signals from rapidly decaying musculoskeletal tissues. Rapid imaging may be desirable for patients who have joint or bone pain, and the efficiency of spiral readouts in accordance with embodiments of the present disclosure supports rapid generation of 3D UTE images, achieving whole-head UTE images in 67 s and whole-knee images in 97 s.

Figure 8:
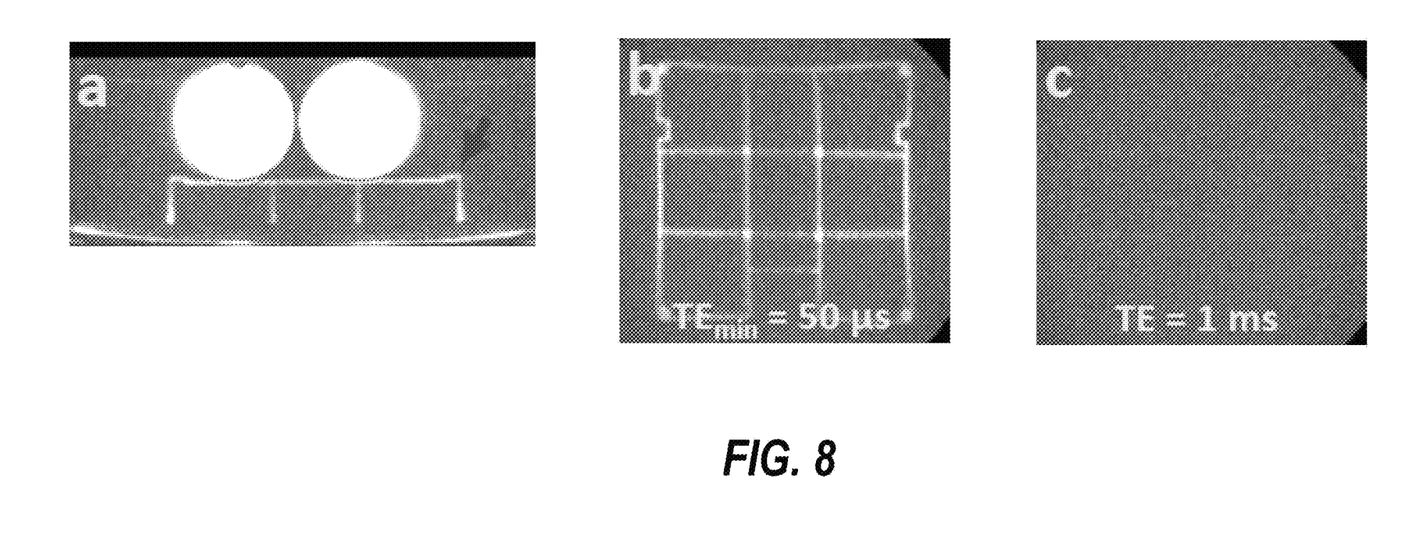
FIG. 8 shows images of a hard-plastic frame, obtained by implementing aspects of the present disclosure in accordance with some embodiments.
Figure 9:
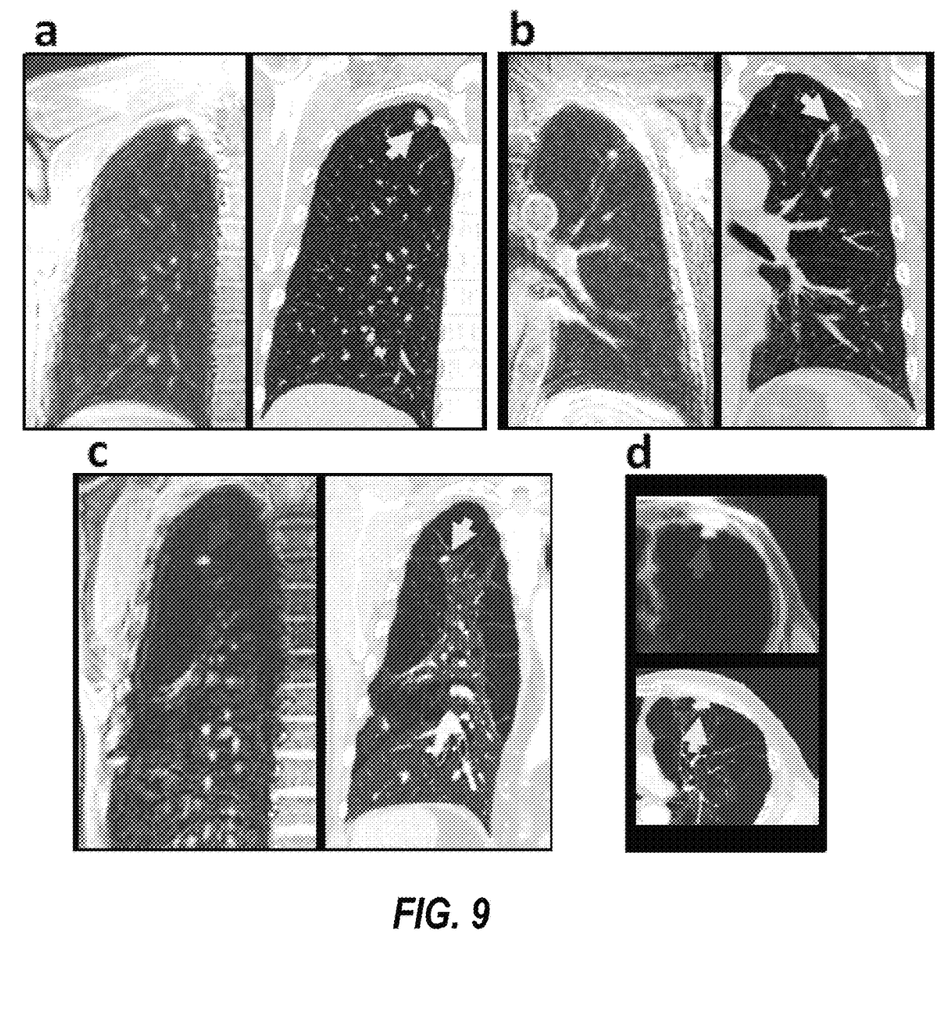
FIG. 9 shows images obtained by implementing aspects of the present disclosure in accordance with some embodiments, including images with pulmonary nodules detected in three subjects with chronic obstructive pulmonary disease (COPD) by MR or CT.

Now referring to FIGS. 8 and 9, in a third example implementation of various aspects of the present disclosure, a commercial version of 3D spoiled gradient-echo imaging was modified to support a stack-of-spirals acquisition for breath-hold UTE imaging of the lungs of human subjects. The modified approach will be referred to in some instances as "spiral UTE VIBE" in describing this example implementation of aspects of the present disclosure. The excitation RF pulse was replaced by a short, rectangular RF waveform, which permitted minimum TE values of less than 100 μs. The basic operation of the pulse sequence was verified using phantoms and healthy subjects, and was tested in three subjects with chronic obstructive pulmonary disease (COPD) who had one or more small lung nodules confirmed on computed tomography (CT). Imaging parameters for the COPD subjects included: TR 4.2 ms; flip angle 5°; matrix 256×256×56; voxel 2×2×5 mm³; 64 interleaves at 2.48 ms each; 15-s acquisition time. The TE (measured from the center of the RF pulse) varied during the acquisition from 50 µs ($TE_{min}$; for PE plane through center of k-space) to 270 µs (for PE planes at edges of k-space). Imaging was performed on a 1.5T scanner (Avanto, Siemens) using body-array and spine-array RF coils.

FIG. 8 illustrates imaging of a hard-plastic frame using spiral UTE VIBE in accordance with one example implementation. In FIG. 8, (a) is an axial spiral UTE VIBE image from a 3D acquisition showing two water bottles on a hard plastic frame (see arrow); (b) is a coronal image through the hard plastic frame for $TE_{min}$=50 µs; and (c) is a coronal image through the hard plastic frame for TE=1 ms. While the frame is clearly seen using $TE_{min}$ 50 µs (see (b)), it is barely visible using a TE of 1 ms (see (c)).

FIG. 9 shows images with pulmonary nodules detected in three subjects (Subject 1 shown at "a"; Subject 2 shown at "b"; and Subject 3 shown at "c" and "d") with COPD by MR (see arrow in leftmost image of each respective set of two images in "a", "b", and "c", and topmost image of the set of two images in "d") or CT (see arrow in rightmost image of each respective set of two images in "a", "b", and "c", and bottommost image of the set of two images in "d"). The nodules detected in each subject include ones in the right apex of subject 1, the left apex of subject 2, and in two locations in subject 3 (right apex, left anterior apex at chest wall). The 6-mm nodule in subject 2 was more conspicuous on MR than CT because of the low signal from the surrounding structures. In addition, the severe emphysema in subject 3 along the periphery of the right lung is apparent on MRI although less conspicuous than on CT. Thus, lung nodules, confirmed on CT, were visible in all three of the COPD subjects; all nodules detected with CT (ranging from approximately 3-mm to 1-cm) were apparent on MRI. Due to the relatively low sensitivity of spiral trajectories to motion and the low flip angle used, no significant motion artifacts were observed from the heart or major vessels.

In these example implementations and results corresponding to FIGS. 8 and 9, breath-hold UTE imaging of the lung has been demonstrated, using, in some embodiments, an optimized 3D stack-of-spirals acquisition, without requiring additional acceleration such as parallel imaging. Among other indications, the results show that implementing various aspects of the present disclosure in accordance with some embodiments can be useful for detection of pulmonary nodules.

The specific configurations, choice of materials and the size and shape of various elements can be varied according to particular design specifications or constraints requiring a system or method constructed according to the principles of the present disclosure. Such changes are intended to be embraced within the scope of the present disclosure. The presently disclosed embodiments, therefore, are considered in all respects to be illustrative and not restrictive. The patentable scope of certain embodiments of the present disclosure is indicated by the appended claims, rather than the foregoing description, and all changes that come within the meaning and range of equivalents thereof are intended to be embraced therein.

What is claimed is:

1. A method for ultrashort-echo-time (UTE) imaging, comprising:
acquiring UTE imaging data associated with an area of interest of a subject, the acquiring comprising applying an imaging pulse sequence with a three-dimensional (3D) spiral acquisition and a nonselective excitation pulse; and
reconstructing at least one image of the area of interest from the acquired UTE imaging data.

2. The method of claim 1, wherein the 3D spiral acquisition comprises a variable echo time (TE) 3D stack-of-spirals acquisition.

3. The method of claim 2, wherein the 3D stack-of-spirals acquisition uses a 3D spoiled gradient-echo sequence.

4. The method of claim 2, wherein the minimum TE is about 50 µs.

5. The method of claim 1, wherein the nonselective excitation pulse is a nonselective hard RF excitation pulse.

6. The method of claim 1, wherein the area of interest of the subject comprises an area of the musculoskeletal system of the subject.

7. The method of claim 1, wherein the area of interest of the subject comprises the lungs of the subject.

8. The method of claim 1, further comprising:
based on the reconstructed at least one image, determining at least one physiological characteristic of the area of interest of the subject.

9. A system for ultrashort-echo-time (UTE) imaging, comprising:
a data acquisition device configured to acquire UTE imaging data associated with an area of interest of a subject, the acquiring comprising applying an imaging pulse sequence with a three-dimensional (3D) spiral acquisition and a nonselective excitation pulse; and
one or more processors coupled to the data acquisition device and configured to cause the system to perform functions comprising:
reconstructing at least one image of the area of interest from the acquired UTE imaging data.

10. The system of claim 9, wherein the data acquisition device comprises a magnetic resonance imaging device.

11. The system of claim 9, wherein the 3D spiral acquisition comprises a variable echo time (TE) 3D stack-of-spirals acquisition.

12. The system of claim 11, wherein the 3D stack-of-spirals acquisition uses a 3D spoiled gradient-echo sequence.

13. The system of claim 11, wherein the minimum TE is about 50 µs.

14. The system of claim 9, wherein the nonselective excitation pulse is a nonselective hard RF excitation pulse.

15. The system of claim 9, wherein the area of interest of the subject comprises an area of the musculoskeletal system of the subject.

16. The system of claim 9, wherein the area of interest of the subject comprises the lungs of the subject.

17. The system of claim 9, wherein the one or more processors coupled to the data acquisition device are configured to cause the system to perform functions that further comprise:
based on the reconstructed at least one image, determining at least one physiological characteristic of the area of interest of the subject.

18. A non-transitory computer-readable medium having stored instructions that, when executed by one or more processors, cause one or more computing devices to perform functions that comprise:
acquiring UTE imaging data associated with an area of interest of a subject, the acquiring comprising applying an imaging pulse sequence with a three-dimensional (3D) spiral acquisition and a nonselective excitation pulse; and reconstructing at least one image of the area of interest from the acquired UTE imaging data.

19. The non-transitory computer-readable medium of claim 18, wherein the 3D spiral acquisition comprises a variable echo time (TE) 3D stack-of-spirals acquisition.

20. The non-transitory computer-readable medium of claim 19, wherein the 3D stack-of-spirals acquisition uses a 3D spoiled gradient-echo sequence.

21. The non-transitory computer-readable medium of claim 19, wherein the minimum TE is about 50 μs.

22. The non-transitory computer-readable medium of claim 18, wherein the nonselective excitation pulse is a nonselective hard RF excitation pulse.

23. The non-transitory computer-readable medium of claim 18, wherein the area of interest of the subject comprises an area of the musculoskeletal system of the subject.

24. The non-transitory computer-readable medium of claim 18, wherein the area of interest of the subject comprises the lungs of the subject.

25. The non-transitory computer-readable medium of claim 18, wherein the stored instructions, when executed by the one or more processors, cause the one or more computing devices to perform functions that further comprise:

based on the reconstructed at least one image, determining at least one physiological characteristic of the area of interest of the subject.

* * * * *